United States Patent
Wulf

(10) Patent No.: US 9,255,341 B2
(45) Date of Patent: Feb. 9, 2016

(54) METHOD, APPARATUS, AND ELECTROLYTIC SOLUTION FOR ELECTROPOLISHING METALLIC STENTS

(71) Applicant: Abbott Laboratories Vascular Enterprises Limited, Dublin (IE)

(72) Inventor: Elena Wulf, Burladingen (DE)

(73) Assignee: ABBOTT LABORATORIES VASCULAR ENTERPRISES LIMITED, Dublin (IE)

(*) Notice: Subject to any disclaimer, the term of this patent is extended or adjusted under 35 U.S.C. 154(b) by 91 days.

(21) Appl. No.: 14/135,279

(22) Filed: Dec. 19, 2013

(65) Prior Publication Data

US 2014/0110272 A1    Apr. 24, 2014

Related U.S. Application Data

(60) Division of application No. 12/840,055, filed on Jul. 20, 2010, now Pat. No. 8,647,496, which is a continuation-in-part of application No. PCT/EP2010/000216, filed on Jan. 15, 2010, which is (Continued)

(30) Foreign Application Priority Data

Jul. 15, 2010 (EP) .................................. 10007363

(51) Int. Cl.
    C25F 3/16      (2006.01)
    C25F 7/00      (2006.01)
    A61L 31/14     (2006.01)

(52) U.S. Cl.
    CPC . C25F 3/16 (2013.01); A61L 31/14 (2013.01); C25F 7/00 (2013.01); A61L 2400/18 (2013.01)

(58) Field of Classification Search
    USPC ....................................................... 205/676
    See application file for complete search history.

(56) References Cited

U.S. PATENT DOCUMENTS

| | | | |
|---|---|---|---|
| 3,190,822 | A | 6/1965 | Burnham |
| 4,613,417 | A | 9/1986 | Laskowski et al. |
| 5,049,477 | A | 9/1991 | Nakamura et al. |
| 5,242,492 | A | 9/1993 | Krivohlavek |

(Continued)

FOREIGN PATENT DOCUMENTS

| | | |
|---|---|---|
| GB | 821229 | 10/1959 |
| GB | 1357978 | 6/1974 |

(Continued)

OTHER PUBLICATIONS

U.S. Appl. No. 61/145,453, filed Jan. 16, 2009, Wulf.

(Continued)

*Primary Examiner* — Nicholas A Smith
(74) *Attorney, Agent, or Firm* — Workman Nydegger; John Kwok

(57) ABSTRACT

An apparatus, a method, and an electrolytic solution are described for electropolishing metallic stents made, for example, of high-strength medical alloys. The apparatus may include an electropolishing container made from material of low thermal conductivity. The apparatus may include at least one spiral cathode for optimization of solution agitation and/or voltage distribution in the electrolytic solution. Further, an electrolytic solution including at least dimethylsulfate is described. A method for improved electropolishing to consistently produce smooth surfaces is also described.

14 Claims, 1 Drawing Sheet

Related U.S. Application Data a continuation-in-part of application No. PCT/EP2010/000217, filed on Jan. 15, 2010.

(60) Provisional application No. 61/145,453, filed on Jan. 16, 2009, provisional application No. 61/145,460, filed on Jan. 16, 2009.

(56) References Cited

U.S. PATENT DOCUMENTS

| | | |
|---|---|---|
| 6,447,664 B1 * | 9/2002 | Taskovics et al. ............ 205/170 |
| 6,679,980 B1 | 1/2004 | Andreacchi |
| 6,916,409 B1 | 7/2005 | Callol |
| 2005/0045491 A1 | 3/2005 | Zhu et al. |
| 2005/0209117 A1 | 9/2005 | Friedrich |
| 2006/0169597 A1 | 8/2006 | Liu et al. |
| 2007/0209947 A1 | 9/2007 | Shrivastava et al. |
| 2011/0062031 A1 | 3/2011 | Wulf |

FOREIGN PATENT DOCUMENTS

| | | |
|---|---|---|
| WO | WO 01/71068 | 9/2001 |
| WO | WO 2010/081723 | 7/2010 |
| WO | WO 2010/081724 | 7/2010 |

OTHER PUBLICATIONS

U.S. Appl. No. 61/145,460, filed Jan. 16, 2009, Wulf.
Dimethyl Sulfate, url: http://web.archive.org/web/20071230184200/http://en.wikipedia.org/wiki/Dimethyl_sulfate, Dec. 2007.
Van Loon, L.L., et al., "Methanol Reaction With Sulfuric Acid: A Vibrational Spectroscopic Study," *J. Phys. Chem. B*. vol. 108. (2004). p. 17666-17674.
U.S. Appl. No. 12/840,055, filed Jan. 18, 2013, Office Action.
U.S. Appl. No. 12/840,055, filed Apr. 9, 2013, Office Action.
U.S. Appl. No. 12/840,055, filed Oct. 1, 2013, Notice of Allowance.

* cited by examiner

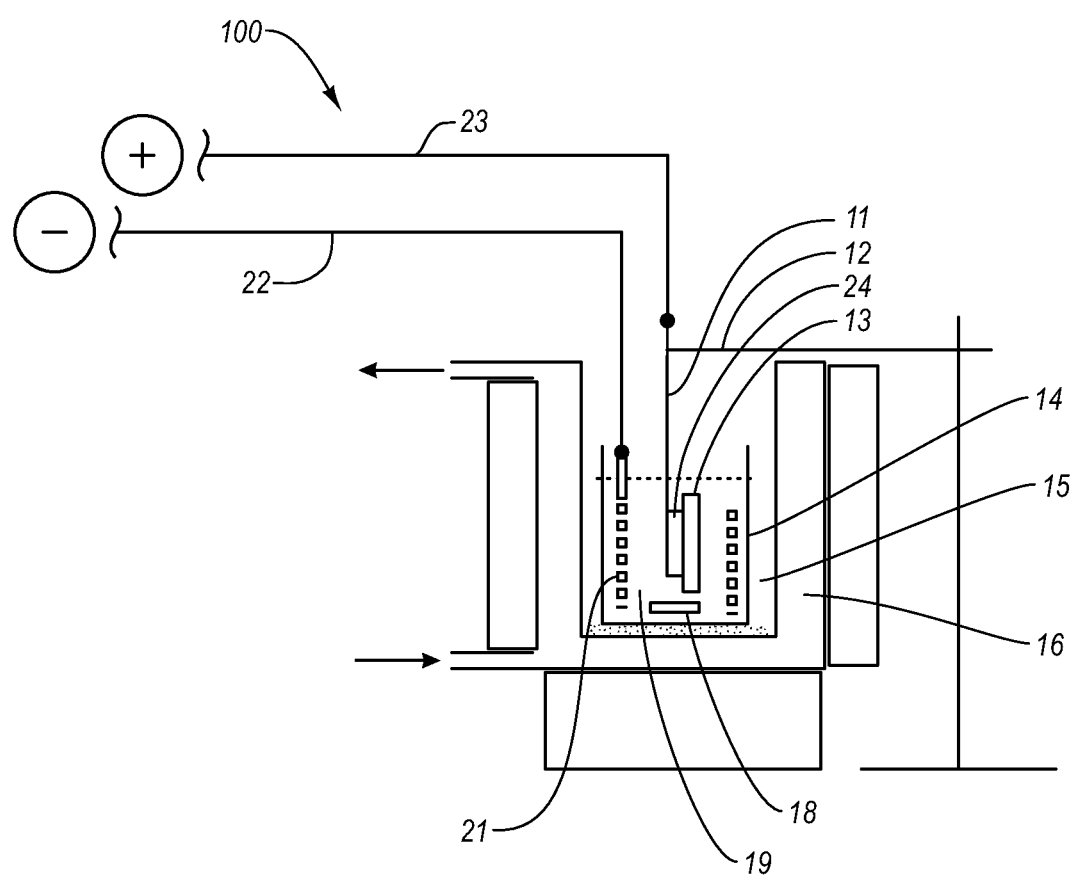

US 9,255,341 B2

METHOD, APPARATUS, AND ELECTROLYTIC SOLUTION FOR ELECTROPOLISHING METALLIC STENTS

CROSS-REFERENCE TO RELATED APPLICATIONS

This application is a divisional application of U.S. patent application Ser. No. 12/840,055, now U.S. Pat. No. 8,647, 496, filed 20 Jul. 2010, which application (i) is a continuation-in-part of International Application No. PCT/EP2010/000216 filed on 15 Jan. 2010, which claims the benefit of U.S Provisional Patent Application No. 61/145,453 filed on 16 Jan. 2009, (ii) is a continuation-in-part of International Application No. PCT/EP2010/000217 filed on 15 Jan. 2010, which claims the benefit of U.S. Provisional Patent Application No. 61/145,460 filed on 16 Jan. 2009, and (iii) claims priority to European Patent Application No. 10 007 363.4 filed on 15 Jul. 2010. Each of the foregoing applications is hereby incorporated herein, in their entireties, by this reference.

BACKGROUND

The present disclosure relates generally to providing an apparatus, a method, and an electrolytic solution for electropolishing products made from metals. In particular, the present disclosure relates generally to electropolishing metallic medical devices (e.g. stents) made of high-strength medical alloys, such as stainless steel, titanium, nickel-titanium, tungsten, tantalum, niobium, cobalt-chromium, cobalt-chromium-tungsten, etc. While the apparatus, method, and electrolytic solution are described herein as being applicable mainly to medical stents, in particular intravascular stents, the disclosure is not limited to such medical products. For example, the methods may be applied to electropolish metallic automotive or aerospace components.

Stents are generally tube-shaped devices placed within a blood vessel or other body lumen to maintain the patency of the lumen and, in some cases, to reduce the development of restenosis. The stents may be formed in a variety of configurations which are typically expandable since they are delivered in a compressed form to a desired site. Such a configuration may be a helically wound wire, wire mesh, weaved wire, serpentine stent, chain of rings, other configuration, or combinations thereof. The walls of stents are typically perforated in a framework design of wire-like connected elements or struts, or in a weave design of cross-threaded wire.

Some stents are made of more than one material. For example, a stent may include a sandwich of metals having outer layers of a biocompatible material, such as stainless steel or cobalt-chromium, with an inner layer providing the radiopacity to the stent for tracking by imaging devices during placement. A stent made of such material may be, for example, a thin layer of titanium between layers of stainless steel or cobalt-chromium. In forming such stents from metal, a roughened outer surface of the stent may result from the manufacturing process. It may be desirable for the surface of the stent to be smooth so that it may be inserted and traversed with reduced friction through the blood vessels or other body lumens toward the site of implantation. A rough outer surface may not only increase frictional obstruction, but may also damage the lining of the vessel wall during insertion. Furthermore, smooth surfaces may reduce thrombus formation and/or corrosion.

Since processing to form metallic stents often results in a product initially having burrs, sharp ends, debris, slag material from melting the metal during processing, other features, or combinations thereof, as a first order treatment of the product, the surface may be descaled in preparation for, for example, further surface treatment such as electropolishing.

An apparatus, a method, and an electrolytic solution is provided for electropolishing stents after they have been descaled, for example, as disclosed in U.S. patent application Ser. No. 11/370,642 filed on 7 Mar. 2006, the disclosure of which is hereby incorporated, in its entirety, by this reference.

Descaling may include, for example, dipping the stent into a strongly acidic solution and/or ultrasonically cleaning the stent.

Electropolishing is an electrochemical process by which some of the surface metal may be electrolytically dissolved. In general, the metal stent serves as an anode and is connected to a power supply while immersed in an electrolytic solution having a metal cathode connected to the negative terminal of the power supply. Current flows from the stent, as the anode, causing it to become polarized. The rate at which the metal ions on the stent are dissolved may be controlled by the applied current and/or voltage. The positioning of the cathode relative to the stent may provide an even distribution of current to the stent. According to the theory of electropolishing, the current density is typically highest at high points protruding from a surface and is typically lowest at the surface low points. Thus, the higher current density at the raised points may cause the metal to dissolve faster at these points, which may level the surface. Electropolishing therefore may smooth the surface, even to the point where it is shiny and reflective.

The present disclosure provides an apparatus, a method, and an electrolytic solution for electropolishing a plurality of metallic devices (e.g., stents) substantially simultaneously to consistently produce smooth surfaces.

SUMMARY

The present disclosure is directed to an apparatus, a method, and an electrolytic solution for electropolishing one or more metallic devices, such as metallic stents. An embodiment of an apparatus is provided for substantially simultaneously electropolishing a plurality of metallic stents. The apparatus may include a plurality of elongated members each having a longitudinal axis, an electrolytic solution, a substantially continuous cathode, a cathode current conducting member, and an anode current conducing member. Each of the elongated members may include an electrically conductive adaptor configured to be removably affixed to and in electrical contact with a metallic stent. The substantially continuous cathode may be configured to be located in close proximity to each of the elongated members when the elongated members and substantially continuous cathode are immersed in the electrolytic solution. The cathode current conducting member is attached to the substantially continuous cathode, and each of the elongated members is conductively connected electrically with the anode current conducting member.

In one embodiment, the substantially continuous cathode has a spiral configuration and/or the electrolytic solution is contained in a container made from non-metallic material. The container may be made from glass, ceramic, plastic, or other materials.

In another embodiment, the apparatus includes a second substantially continuous cathode configured to be located in close proximity to each of the elongated members when the elongated members and cathode are immersed in the electrolytic solution and a second cathode current conducting member attached to the second substantially continuous cathode.

In a further embodiment, the two cathodes are both in the shape of a spiral and are disposed substantially concentrically in the solution.

An embodiment of a method is also provided for electropolishing at least one metallic stent. The method may include:

a) affixing a stent onto a corresponding one of one or more electrically conductive adaptors of an apparatus, the apparatus including:

one or more elongated members having a longitudinal axis, each of the members including an electrically conductive adaptor configured to be removably affixed to and in electrical contact with a metallic stent;

an electrolytic solution;

a substantially continuous cathode configured to be located in close proximity to each of the elongated members when the elongated members and the substantially continuous cathode are immersed in the electrolytic solution;

a cathode current conducting member attached to the substantially continuous cathode;

an anode current conducting member, wherein each of the elongated members is conductively connected electrically with the anode current conducting member;

b) immersing the stent(s) into the electrolytic solution;

c) supplying a voltage difference between the cathode current conducting member and the anode current conducting member; and d) removing the stent(s) from the solution and rinsing with at least one rinsing solution.

In one embodiment, the method further may include e) removing the stents from the apparatus;

f) rinsing the stents;

g) immersing the stents in a passivation solution;

h) removing the stents from the passivation solution and rinsing;

i) placing the stents in a liquid and applying ultrasound energy to the liquid, or combinations thereof.

In another embodiment, in act c) the voltage is supplied for a period in the range of about 20 to about 60 seconds while the stents are immersed in the electrolytic solution.

In a further embodiment, acts b), c), and d) are repeated three to five times.

In one embodiment, the passivation solution includes nitric acid.

In one embodiment, the electrolytic solution comprises at least dimethylsulfate. In some embodiments, the electrolytic solution may not include polyethylene glycol, dimethylsulfate, and ethanol at the same time. In other embodiments, the electrolytic solution may include polyethylene glycol, dimethylsulfate, and ethanol. In other embodiments, the electrolytic solution includes polyethylene glycol, dimethylsulfate, ethanol, and methanol.

In a further embodiment, the electrolytic solution may further include at least one additional component, such as at least one alcohol. For example, the at least one alcohol may be a polyol (e.g., polyethylene glycol) and/or at least one alkyl alcohol (e.g., ethanol, methanol, or mixtures thereof).

In one embodiment, the electrolytic solution may include from about 25 to about 60 weight percent dimethylsulfate, from about 30 to about 40 weight percent dimethylsulfate, from about 35 to about 39 weight percent dimethylsulfate, or about 37 weight percent dimethylsulfate.

In another embodiment, the electrolytic solution may include from about 40 to about 70 weight percent dimethylsulfate, from about 50 to about 60 weight percent dimethylsulfate, from about 54 to about 58 weight percent dimethylsulfate, or about 55 to about 57 weight percent dimethylsulfate.

In one embodiment, the electrolytic solution further comprises polyethylene glycol. The electrolytic solution may include from about 0.1 to about 5 weight percent polyethylene glycol, from about 0.5 to about 2 weight percent polyethylene glycol, or about 0.5 to about 1 weight percent polyethylene glycol. In a further embodiment, the polyethylene glycol is PEG 1000. The electrolytic solution may include polyethylene glycol in any of the disclosed weight percentages along with dimethylsulfate in any of the disclosed weight percentages.

When the electrolytic solution further comprises at least one alkyl alcohol (e.g., ethanol, methanol, or mixtures thereof), the electrolytic solution may include from about 15 weight percent to about 50 weight percent ethanol, from about 20 to about 40 weight percent ethanol, from about 25 to about 35 weight percent ethanol, or about 28 weight percent ethanol. In one embodiment, the balance of the electrolytic solution containing at least one alkyl alcohol (e.g., ethanol) is made up of methanol.

These and other objects and features of the present disclosure will become more fully apparent from the following description and appended claims, or may be learned by the practice of the disclosure as set forth hereinafter.

BRIEF DESCRIPTION OF THE DRAWINGS

To further clarify the above and other advantages and features of the present disclosure, a more particular description of the disclosure will be rendered by reference to specific embodiments thereof which are illustrated in the appended drawing. It is appreciated that this drawing depicts only illustrated embodiments of the disclosure and are therefore not to be considered limiting of its scope. The disclosure will be described and explained with additional specificity and detail through the use of the accompanying drawing in which:

FIG. 1 is a diagrammatic view of an electropolishing apparatus showing at least one stent immersed in an electrolytic solution and in close proximity to the cathode according to an embodiment of the present disclosure.

DETAILED DESCRIPTION

The present disclosure is directed to an apparatus, a method, and an electrolytic solution for electropolishing one or more metallic devices, such as metallic stents. One or more embodiments of the present disclosure may advantageously provide a very easy and simple way to electropolish such devices to impart a high degree of smoothness in the electropolished device while allowing substantially simultaneously electropolishing of a plurality of such devices. Furthermore, by providing a spiral cathode in an electropolishing container made from a material with low thermal conduction, the electrolyte solution may remain stable for an extended time.

In one embodiment, an apparatus for electropolishing one or more stents includes a spiral cathode in an electropolishing container made from a material with low thermal conduction. The electrolyte solution may remain stable for an extended time in such an apparatus. In a more detailed embodiment, the apparatus includes two concentric spiral cathodes with the one or more stents, as anodes, placed therebetween, thereby providing additional cathode surface area. The pitch of the spiral can be varied in order to balance good agitation of the electrolytic solution in the polishing container to ensure continuous electrolyte concentration and composition and provision of a high surface area of the cathode.

In another embodiment, an improved electrolytic solution comprising at least dimethylsulfate for improved electropolishing of metallic medical devices, such as stents, is also described.

Referring to FIG. 1, there is shown an embodiment of an apparatus 100 according to the disclosure. The apparatus 100 may include at least one elongated member 11 in a downward orientation along a longitudinal axis. Each of the elongated members 11 may accommodate an electrically conductive adapter 24 which may be capable of being removably affixed to and/or in electrical contact with a metallic stent 13.

With the at least one elongated member 11 immersed in electropolishing solution 19 contained in a container 14, a tubular substantially continuous spiral cathode 21 may be in close proximity with the at least one elongated members 11. Each elongated member 11 may be substantially equidistant from the facing surface of the cathode 21. This may provide a consistent field to each of the stents 13. The cathode 21 may be attached to a cathode conducting member 22. The at least one stent 13, as anodes, attached to the elongated member(s) 11 may all be in electrical connection in series and/or in parallel with an anode current conducting member 23. The cathode conducting member 22 and/or the anode conducting member 23 may be connected to an electromotive force ("EMF")-providing DC source (e.g., a battery) from which current and/or voltage may be controlled by an appropriate controller. The entire system may be placed into a polishing container 14 made from material with a low thermal conduction. Suitable materials for the polishing container 14 may include glass, ceramic, plastic, or other materials.

The polishing container 14 may contain an electrolytic electropolishing solution 19 and/or may be placed in a double walled reaction container 16. The polishing container 14 may be cooled with a cooling solution 15, such as ethanol or other suitable cooling solution. Using the polishing container 14 made from material with low thermal conduction may reduce water condensation at the wall portions of the polishing container exposed to, for example, air. Dilution of the electropolishing solution 19 by water condensing out of the air may be reduced potentially resulting in the electropolishing solution 19 that may be stable and/or reliable and/or may provide constant polishing results. To facilitate agitation of the electropolishing solution 19 during the electropolishing process, a stirrer 18, such as a magnetic stirrer may be placed into the polishing container 14.

Examples of suitable stents for the stents 13 include, but are not limited to, coronary and endovascular stents. Typical coronary and/or endovascular stents may vary in a range from about 7 to up to about 200 millimeters in length with a diameter in a range of about 1 to about 12 millimeters. However, stents of larger or smaller size may be suitably accommodated. The stents 13 may be made from high-strength medical alloys, such as stainless steel, titanium alloys, nickel-titanium alloys, tungsten or a tungsten alloy, tantalum or a tantalum alloy, niobium or a niobium alloy, cobalt-chromium alloys, cobalt-chromium-tungsten alloys, combinations of any of the foregoing, or another suitable metal or alloy.

In order to accomplish the electropolishing process, the one or more stents 13, which may all be substantially identical in length, diameter, design, or combinations thereof, may be placed on the one or more electrically conductive adaptors 24. The mounted stents 13 may be immersed into the electropolishing solution 19. The temperature of the electropolishing solution may be between about −20° C. and about 0° C., between about −20° C. and about −10° C., or about −15° C. A voltage is supplied to the stents 13, as anodes, and the cathode 21 to electropolish the stents 13 to the desired smoothness. Useful voltage may be in the range of about 7 volts to about 40 volts, between about 10 volts and about 30 volts, or between about 10 volts and about 20 volts. Voltage may be applied in about 20 second to about 60 second intervals and, in some embodiments, in about 30 second intervals. However, voltages outside of these ranges may also be useful, depending upon the number of stents, electrolyte, and/or other design and/or process parameters.

It may be desirable for the electropolishing process to be performed in stages. After one immersion in the electropolishing solution 19, typically lasting from about 20 to about 60 seconds, the stents 13 may be removed from the electropolishing solution 19 and washed, typically with alcohol, water, nitric acid, or combinations thereof. Then, the electropolishing may be repeated several times with each step followed by a rinse of the stents 13. Typically, a suitable polishing process will include about three to about five iterations of the electropolishing step. But more or fewer iterations may be suitable, depending upon the stents, electrolyte, voltage, other process variations, or combinations thereof. Once the desired electropolishing is completed, the stents 13 may be removed from the electropolishing solution and from the electropolishing apparatus 100, rinsed, and contacted with a passivation solution to remove residual electropolishing solution. The stents 13 are typically again rinsed and placed in a bath to which ultrasound energy may be applied to complete the rinsing. A final rinse step may involve exposure for about 10 minutes in an ultrasound bath at approximately room temperature.

Embodiments of an electrolytic solution for electropolishing one or more metallic stents for use in the methods and apparatuses described above are also disclosed. The electrolytic solution for use in the methods described above comprises at least dimethylsulfate.

In some embodiments, the electrolytic solution may not include polyethylene glycol, dimethylsulfate, and ethanol at the same time. In other embodiments, the electrolytic solution includes polyethylene glycol, ethanol, and dimethylsulfate. In other embodiments, the electrolytic solution includes polyethylene glycol, dimethylsulfate, ethanol, and methanol.

In a further embodiment, the electrolytic solution includes from about 25 to about 60 weight percent dimethylsulfate, from about 30 to about 40 weight percent dimethylsulfate, from about 35 to about 39 weight percent dimethylsulfate, or about 37 weight percent dimethylsulfate. Such weight percentages of dimethylsulfate are more typical when both ethanol and methanol are present in the electrolytic solution.

In one embodiment, the electrolytic solution may further include at least one additional component, such as at least one alcohol. For example, the at least one alcohol may be a polyol (e.g., polyethylene glycol) and/or at least one alkyl alcohol (e.g., ethanol, methanol, or combinations thereof). In an embodiment, the polyethylene glycol is PEG 1000.

In a further embodiment, the electrolytic solution may include from about 0.1 to about 5 weight percent polyethylene glycol, from about 0.5 to about 2 weight percent polyethylene glycol, or about 0.5 to 1 weight percent polyethylene glycol.

In one embodiment, the electrolytic solution includes from about 15 to about 50 weight percent ethanol, from about 20 to about 40 weight percent ethanol, from about 25 to about 35 weight percent ethanol, from about 25 to about 30 weight percent ethanol or about 28 weight percent ethanol. In some embodiments, the ethanol may be replaced with methanol, a mixture of ethanol and methanol, or other alkyl alcohol. In some embodiments, the balance of the electrolytic solution is made up of methanol.

In a more specific embodiment, the electrolytic solution includes from about 0.1 to about 5 weight percent polyethylene glycol, from about 0.5 to about 2 weight percent polyethylene glycol, or from about 0.5 to about 1 weight percent polyethylene glycol, with the polyethylene glycol being PEG 1000; from about 25 to about 60 weight percent dimethylsulfate, from about 30 to about 40 weight percent, from about 35 to about 39 weight percent, or about 37 weight percent; from about 15 to about 50 weight percent ethanol, from about 20 to about 40 weight percent, from about 25 to about 35 weight percent, from about 25 to about 30 weight percent, or about 28 weight percent; and a balance of methanol.

In another embodiment, the electrolytic solution includes from about 40 to about 70 weight percent dimethylsulfate, from about 50 to about 60 weight percent dimethylsulfate, from about 54 to about 58 weight percent dimethylsulfate, or about 56 weight percent dimethylsulfate. Such weight percentages may be more typical in electrolytic solutions that include dimethylsulfate, polyethylene glycol, a balance of ethanol, and are substantially free of methanol.

In a more specific embodiment, the electrolytic solution includes from about 0.1 to about 5 weight percent polyethylene glycol, from about 0.5 to 2 weight percent polyethylene glycol, or about 1 weight percent polyethylene glycol, with the polyethylene glycol being PEG 1000; from about 40 to about 70 weight percent dimethylsulfate, from about 50 to about 60 weight percent, from about 54 to about 58 weight percent, from about 55 to about 57 weight percent, or about 56 to about 57 weight percent; and a balance of ethanol.

The following examples are presented for the purpose of illustration and are not intended to limit the disclosure and claims in any way.

EXAMPLE 1

Four dry identical stents made from a high-strength medical alloy may be removably affixed to the adapters of four elongated members. While agitating a electropolishing solution of polyethylene glycol (PEG 1000):dimethylsulfate:ethanol:methanol in a weight ratio of about 1:59:44:54, (i.e., 0.6 weight percent polyethylene glycol (PEG 1000), 37.3 weight percent dimethylsulfate, 27.9 weight percent ethanol and 34.2 weight percent methanol), the stents are lowered on the apparatus into the electropolishing solution. The positive lead from the electrical source is attached to the apparatus and the magnetic stirrer in the electropolishing container is turned on to facilitate agitation of the electropolishing solution. When the cycle time has elapsed (depending on the size and type of stent), the stents are removed from the electropolishing solution and submerged in a container of ethanol. Each stent is moved while submerged. The stents are then re-immersed in the electropolishing solution for another polishing cycle. The polishing cycle is repeated for four polishing cycles. The stents are removed from the adapters and placed into a purified water rinse for about 30 seconds. The stents are then removed and placed in nitric acid passivation rinse bath for 30 minutes. The stents are removed from the bath and placed in a purified water ultrasonic bath for about 10 minutes. The stents are then removed from the bath, rinsed with alcohol and are dried with compressed air. The stents achieve a very high degree of smoothness.

EXAMPLE 2

Four dry identical stents may be removably affixed to the adapters of four elongated members. While agitating an electropolishing solution of polyethylene glycol (PEG 1000): dimethylsulfate:ethanol in a weight ratio of about 1:59:44 (i.e., about 1 weight percent polyethylene glycol (PEG 1000), 57 weight percent dimethylsulfate, 42 weight percent ethanol), the stents are lowered on the apparatus into the electropolishing solution. The positive lead from the electrical source is attached to the apparatus and the magnetic stirrer in the electropolishing container is turned on to facilitate agitation of the electropolishing solution. When the cycle time has elapsed (depending on the size and type of stent), the stents are removed from the electropolishing solution and submerged in a container of ethanol. Each stent is moved while submerged. The stents are then re-immersed in the electropolishing solution for another polishing cycle. The polishing cycle is repeated for four polishing cycles. The stents are removed from the adapters and placed into a purified water rinse for about 30 seconds. The stents are then removed and placed in nitric acid passivation rinse bath for 30 minutes. The stents are removed from the bath and placed in a purified water ultrasonic bath for about 10 minutes. The stents are then removed from the bath, rinsed with alcohol and are dried with compressed air.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A method of electropolishing metallic stents, the method comprising:
    a) affixing a stent on a respective one of one or more electrically conductive adaptors of an apparatus, the apparatus comprising:
        at least one elongated member having a longitudinal axis, the at least one elongated member comprising one of the one or more electrically conductive adaptors configured to be removably affixed to and in electrical contact with the stent;
        an electrolytic solution comprising at least dimethylsulfate;
        a substantially continuous cathode configured to be located in close proximity to the at least one elongated member when the least one elongated member and the substantially continuous cathode are immersed in the electrolytic solution;
        a cathode current conducting member attached to the substantially continuous cathode;
        an anode current conducting member, wherein each of the one or more elongated members is conductively connected electrically with the anode current conducting member;
    b) immersing the at least one stent in the electrolytic solution;
    c) supplying a voltage difference between the cathode current conducting member and the anode current conducting member; and
    d) removing the at least one stent from the electrolytic solution and rinsing with alcohol.

2. The method according to claim 1, further comprising repeating acts b), c), and d).

3. The method according to claim 1, wherein the acts b), c), and d) are repeated three to five times.

4. The method according to claim 1, further comprising:
e) removing the at least one stent from the apparatus;
f) rinsing the at least one removed stent;
g) immersing the at least one rinsed stent in a passivation solution;
h) removing the at least one passivated stent from the passivation solution and rinsing the at least one passivated stent; and
i) placing the at least one rinsed and passivated stent in a liquid and applying ultrasound energy to the liquid.

5. The method according to claim 4, wherein the passivation solution comprises nitric acid.

6. The method according to claim 4, wherein the ultrasound energy is applied to the liquid at room temperature.

7. The method according to claim 1, wherein the electrolytic solution further comprises at least one alcohol selected from the group consisting of propylene glycol, ethanol, and methanol.

8. A method of electropolishing at least one stent, comprising:

immersing the at least one stent in an electrolytic solution, wherein the electrolytic solution comprises dimethylsulfate; and
electropolishing the at least one stent while the at least one stent is immersed in the electrolytic solution.

9. The method of claim 8, wherein the electrolytic solution comprises polyethylene glycol, ethanol, and methanol.

10. The method of claim 8, wherein the electrolytic solution comprises polyethylene glycol and ethanol.

11. The method of claim 7, wherein the electrolytic solution does not include polyethylene glycol, dimethylsulfate, and ethanol at the same time.

12. The method of claim 7, wherein the electrolytic solution comprises mixtures of ethanol and methanol.

13. The method of claim 9, wherein the electrolytic solution may not include polyethylene glycol, dimethylsulfate, and ethanol at the same time.

14. The method of claim 9, wherein the electrolytic solution comprises mixtures of ethanol and methanol.

* * * * *